United States Patent [19]
Joly et al.

[11] Patent Number: 5,475,184
[45] Date of Patent: * Dec. 12, 1995

[54] PARAFFIN ALKYLATION CATALYST

[75] Inventors: Jean-Francois Joly, Paris; Nathalie Ferrer, Chatou; Jean-Yves Bernhard, Mennecy; Eric Benazzi, Montesson, all of France

[73] Assignee: Institut Francais Du Petrole, Rueil Malmaison, France

[*] Notice: The portion of the term of this patent subsequent to Aug. 9, 2011, has been disclaimed.

[21] Appl. No.: 230,467

[22] Filed: Apr. 20, 1994

[30] Foreign Application Priority Data

Apr. 20, 1993 [FR] France ................... 93/04.735

[51] Int. Cl.$^6$ ........................... C07C 2/62
[52] U.S. Cl. ............... 585/730; 502/202; 502/216; 585/731; 585/726
[58] Field of Search ............... 585/730, 731, 585/726; 502/202, 216

[56] References Cited

U.S. PATENT DOCUMENTS

| | | | |
|---|---|---|---|
| 2,434,833 | 1/1940 | Clapetta | 585/731 |
| 3,970,721 | 7/1976 | Brockington et al. | 585/731 |
| 4,038,212 | 7/1977 | Brockington et al. | 252/436 |
| 5,220,095 | 6/1993 | Hommeltoft et al. | 585/731 |
| 5,233,119 | 8/1993 | Kallenbach et al. | 585/731 |
| 5,292,986 | 3/1994 | Abbott | 585/731 |
| 5,336,833 | 8/1994 | Joly et al. | 585/731 |

FOREIGN PATENT DOCUMENTS

| | | |
|---|---|---|
| 711745 | 6/1965 | Canada ................... 585/731 |
| 0433954 | 6/1991 | European Pat. Off. . |
| 2682891 | 4/1993 | France . |
| 2683739 | 6/1993 | France . |

OTHER PUBLICATIONS

*The Aldrich Catalog* pp. 1250–1251.

Primary Examiner—Asok Pal
Attorney, Agent, or Firm—Millen, White, Zelano & Branigan

[57] ABSTRACT

Catalyst comprising a porous mineral or organic support and a mixture constituted by sulphuric acid, trifluoromethanesulphonic acid and, optionally, water. The invention also relates to a method for the preparation of the catalyst and its use in catalytic alkylation of isobutane and/or isopentane in the presence of at least one olefin comprising 3 to 6 carbon atoms per molecule.

14 Claims, No Drawings

PARAFFIN ALKYLATION CATALYST

The present invention concerns a catalyst comprising a porous mineral or organic support, preferably silica, and a mixture constituted by sulphuric acid, trifluoromethanesulphonic acid and, optionally, water, a method for its preparation and its use in catalytic alkylation of isobutane and/or isopentane with at least one olefin to obtain at least one product from the group constituted by dimethylbutanes, trimethylpentanes, trimethylhexanes and trimethylheptanes.

Internal combustion engines with spark ignition, especially those with a high compression ratio, are known to require high octane fuels, ie, those constituted mainly by highly branched paraffin hydrocarbons. Such products can be obtained by alkylation of isoparaffins (isobutane and/or isopentane) with olefins containing 3 to 6 carbon atoms per molecule. This reaction requires the use of very acidic catalysts, primarily to reduce side reactions such as olefin hydride abstraction and polymerisation reactions which result in low octane, less branched hydrocarbons and unsaturated hydrocarbons, cracking reactions and dismutation reactions.

Existing processes for the production of hydrocarbon by alkylation of isobutane with olefins employ either sulphuric or hydrofluoric acid catalysts. The acid catalyst in these processes constitute a liquid phase which is brought into contact with the liquid isobutaneolefin(s) mixture to produce an emulsion. These processes are expensive and pose considerable problems regarding personnel and environmental safety. Catalytic systems other than those using liquid phase sulphuric acid and hydrofluoric acid have therefore been studied to attempt to resolve these problems.

Acid catalysts based on a number of solid acids of various types have been developed to catalyse alkylation reactions of isoparaffins with olefins. The following families of acid catalysts may be cited: molecular sieves (see, for example, U.S. Pat. Nos. 3,251,902, 3,647,916, 4,377,721, 4,384,161 and 4,300,015), macroreticular resins which may be associated with $BF_3$ (see, for example, U.S. Pat. Nos. 3,855,342, 3,855,343, 3,862,258 and 3,879,489), Lewis and/or Brönsted acids deposited on various inorganic supports (see, for example, U.S. Pat. Nos. 3,975,299, 3,852,371 and 3,979,476), chlorinated alumina (see, for example, U.S. Pat. Nos. 3,240,840, 3,607,859, 4,066,716 and 4,083,800), graphites interposed with Lewis and/or Brönsted acids (see, for example, U.S. Pat. Nos. 4,083,885, 4,116,880, 4,128,596 and 3,976,714) and anions deposited on oxide supports such as $ZrO_2/SO_4$ (see, for example, J-01 245 854-A, J-01 245 853 and J-61 242 641-A). These solids produce branched isoparaffins but have several major drawbacks, among which are the frequent need to use very high isobutane/olefin molar ratios to limit the impact of secondary reactions and low catalytic activity duration (deposition of unsaturated oligomers inhibiting the catalyst). These catalysts must therefore frequently be regenerated. In addition, the low acidity of some solid acids, such as molecular sieves, necessitates the use of high reaction temperatures which is detrimental to high octane hydrocarbons production.

European patent application EP-A-0 433 954 claims the use of fluorosulphonic acids, namely $FSO_3H$ and $CF_3SO_3H$ acids, for the alkylation reaction of isobutane with olefins in a fixed bed. In one of the examples, the authors show that sulphuric acid produces very bad results when used under the conditions employed in accordance with this invention.

European patent application EP-A-0 539 277 describes a catalyst comprising silica and sulphuric acid in the solid state, the silica having been impregnated with a solution comprising sulphuric acid and an optional additive, namely trifluoromethanesulphonic acid, $CF_3SO_3H$.

French patent application 92/15696 describes a catalyst comprising a porous organic or mineral support, preferably silica, and an equimolar mixture constituted by anhydrous trifluoromethanesulphonic and sulphuric acids.

We have discovered a novel catalyst which can be used to obtain high octane, highly branched paraffin compounds by alkylation of isobutane and/or isopentane with at least one olefin comprising 3 to 6 carbon atoms per molecule. Advantageously, this novel catalyst is used in the reactor in the liquid phase and mixed with the isoparaffin and/or isopentane mixture. The catalyst of the invention may be used in an expanded bed, a perfectly stirred reactor or on a circulating bed.

The catalyst of the present invention comprises a porous organic or mineral support, preferably silica, and a mixture constituted by sulphuric acid, trifluoromethanesulphonic acid and, optionally, water, the support being partially or totally impregnated with said mixture.

Said mixture has a composition by weight between the following limits:

Sulphuric acid: between 80 and 99.5%, preferably between 85 and 99.5%,

Trifluoromethanesulphonic acid: between 0.5 and 15%, preferably between 0.8 and 15%, Water: between 0 and 5%, preferably between 0.05 and 3%.

A silica support may contain impurities such as oxides, alkalis, alkaline-earths, aluminium compounds or any other impurity known to the skilled person, the total amount of impurities not exceeding 2% by weight with respect to the silica. A number of silica sources may be used. The specific surface area of the organic or mineral support is between 0.01 and 1500 $m^2/g$, preferably between 0.01 and 150 $m^2/g$. The total pore volume of said support is between 0.005 and 3 $cm^3/g$, preferably between 0.005 and 1.5 $cm^3/g$ and most preferably between 0.005 and 0.8 $cm^3/g$. Preferably, said support is constituted by substantially spherical particles having a diameter of between 5 and 150 µm, preferably between 5 and 110 µm, most preferably between 5 and 80 µm.

During impregnation of the mineral or organic support, the mixture constituted by sulphuric acid, trifluoromethanesulphonic acid and water occupies a fraction of the total pore volume of between 5 and 100%, preferably between 80 and 100%, and most preferably between 90 and 100%. The catalyst obtained is characterised by a specific surface area of between 0.01 and 500 $m^2/g$, preferably between 0.01 and 150 $m^2/g$ and most preferably between 0.01 and 40 $m^2/g$.

The preferred catalyst preparation method in accordance with the invention comprises the following three steps, where the order of the first two steps may be reversed:

In a first step, the mixture constituted by sulphuric acid, trifluoromethanesulphonic acid and, optionally water is prepared, for example by slow addition with stirring of trifluoromethanesulphonic acid to the solution comprising all the sulphuric acid and optionally water. The overall trifluoromethanesulphonic acid injection period is typically between a few minutes and one hour. Preparation and storage of this mixture must be effected in the absence of moisture.

In a second step, the organic or mineral support is calcined at a temperature generally above 50° C., preferably above 80° C. and most preferably between 200° C. and 600° C., for example at about 500° C. This calcination step normally takes between 10 minutes and 50 hours. Calcination may be carried out in the presence of air or an air/nitrogen mixture, with a flowrate of between 0.001 and 10 l/h/g.

The third step consists in impregnating the calcined porous organic or mineral support with the mixture constituted by sulphuric acid, trifluoromethanesulphonic acid and optionally water. This step may be carried out using any technique known to the skilled person. When stored in the absence of water, the catalyst of the present invention is thus constituted by a porous organic or mineral support impregnated by the mixture constituted by sulphuric acid, trifluoromethanesulphonic acid and optionally water.

The catalyst is used in an alkylation process wherein feedstock comprising at least one isoparaffin, preferably at least one element selected from the group formed by isobutane and isopentane, most preferably by isobutane, and at least one olefin containing 3 to 6 carbon atoms per molecule is treated in the presence of a catalyst constituted by a porous organic or mineral support impregnated with the mixture constituted by sulphuric acid, trifluoromethanesulphonic acid and optionally water.

The isoparaffin(s)-olefin(s) mixture may be introduced into the reactor at a flowrate, expressed as the weight of olefin introduced per weight unit of catalyst per hour of between 0.001 and 10 $h^{-1}$ preferably between 0.002 and 2 $h^{-1}$. Mixing of said mixture may also be effected within the reactor. In each case the mixture produced is in the reactor under temperature and pressure conditions designed to ensure that the hydrocarbon mixture remains liquid on the catalyst.

The reaction temperature may be between −50° C. and 150° C., however catalytic performance is considerably improved when the reaction temperature is below 0° C. The reaction temperature is generally below 0° C., preferably at −3° C. The reactor pressure is such that the hydrocarbons are kept in the liquid state in the reactor.

To limit secondary reactions, an excess of isoparaffin(s) over olefin(s) may be employed. By way of example, when alkylating isobutane with a butene, the isobutane may be introduced pure into the feedstock or as a mixture of butanes containing, for example, at least 40% isobutane. In addition, a pure butene or a mixture of isomeric butenes may be introduced. In each case, the isobutane/butenes molar ratio in the feedstock is generally between 1 and 100, preferably between 3 and 50 and most preferably between 5 and 10.

The reaction products may be regularly monitored by measurement of the bromine number, for example in accordance with French Standard Pr M 07 071, March 1969.

If the nature of the catalyst and its operating conditions are carefully selected, (in particular the temperature), the catalyst of the invention can produce alkylation products of isoparaffin(s) with olefin(s) which are of interest as engine fuels and petrol constituents. The alkylation products obtained preferably comprise at least 60 mole % of paraffins having 8 carbon atoms per molecule and at least 1 mole % of unsaturated compounds, the paraffins having 8 carbon atoms per molecule comprising 70 to 98 mole % of trimethylpentane(s).

A further advantage of the catalyst of the invention is the possibility of alkylating isobutane at low temperature with mixtures of olefins comprising 3 to 6 carbon atoms per molecule, where the proportion of olefins comprising more than 4 carbon atoms per molecule is very high.

The following examples illustrate the invention without in any way limiting its scope.

EXAMPLE 1

Catalyst preparation (a) Catalyst according to the invention: catalyst A 16 g of macroporous silica with a specific surface area of 40 $m^2$/g, a total porous volume of 1.2 $cm^3$/g and principally constituted by substantially spherical particles with an average diameter of 110 μm was activated by calcination in air for 4 hours at 500° C.

The activated silica was stored under argon. 14 g of the dehydrated silica was then dry impregnated, in the absence of moisture, with 22 g of a mixture constituted by:

18.7 g of a solution containing 99% by weight of $H_2SO_4$ and 1% by weight of water, 3,3 g of a solution containing 3.23 g of the acid $CF_3SO_3H$ and 0.07 g of water.

The composition by weight of the acid phase was as follows:

| | |
|---|---|
| $H_2SO_4$ | 84.15% |
| $CF_3SO_3H$ | 14.68% |
| $H_2O$ | 1.17% |

The solid obtained was stored under argon at −18° C.

(b) Catalyst not according to the invention: catalyst B 14 g of dehydrated silica was prepared in identical fashion to that of the catalyst in accordance with the invention. 14 g of said silica was then dry impregnated, in the absence of moisture, with 22 g of a mixture constituted by:

21.78 g of $H_2SO_4$ and 0.22 g of water.

The solid obtained was stored under argon at −18° C.

EXAMPLE 2

Results of isobutane alkylation tests using 1-butene

Catalysts A and B were used to alkylate isobutane with 1-butene to produce high octane branched paraffins. Catalysts A and B were tested using the operating protocol described above.

36 g of catalyst A or B prepared in example 1 was introduced into a 360 ml volume Fischer & Porter glass reactor which had been purged with argon. The reactor containing the catalyst was then closed, placed under a low vacuum, then cooled to a temperature of −20° C.

100 $cm^3$ of isobutane was then added with stirring to the reactor containing the catalyst, said reactor being immersed in a cold bath at −6° C. The catalyst plus isobutane system was stirred for 30 minutes to homogenise the temperature.

A mixture of isobutane and 1-butene containing 20 weight % of 1-butene was added continuously over a total period of 8 hours, the reactor temperature being held at −5° C. throughout the injection period. The volume flowrate of 1-butene was 10 ml/h.

After reacting, the hydrocarbon phase was drawn from the reactor and the isobutane was slowly evaporated off. The alkylate was recovered and analysed using gas chromatography. The composition by weight is given in the table below. The olefin was 100% converted.

|   | CATALYST A | CATALYST B |
|---|---|---|
| $C_5$–$C_7$ | 2.5 | 11.7 |
| $C_8$ total | 93 | 62.1 |
| $C_{9+}$ | 4.5 | 26.2 |
| TMPs/$C_8$ | 94 | 87 |

TMPs/$C_8$: proportion of trimethylpentanes (isomers 224, 223, 234 and 233) in the $C_8$ fraction.

This table shows the effect of the presence of the $CF_3SO_3H$ acid in the catalyst: at the same 1-butene flowrate, a much higher proportion of trimethylpentanes was obtained using catalyst A in accordance with the invention compared with reference catalyst B which did not contain $CF_3SO_3H$ acid. Catalyst A was more active and selective than reference catalyst B.

We claim:

1. Catalyst comprising a macroporous silica support and an acidic mixture consisting essentially of sulphuric acid, trifluoromethanesulphonic acid and optionally, water, the support being impregnated by said mixture and, before impregnation, having a specific surface area of between 0.01 and 1500 m²/g, a total pore volume of between 0.005 and 3 cm³/g and being principally constituted by substantially spherical particles having an average diameter of between 5 to 150 μm, said mixture having a composition by weight between the following limits:

sulphuric acid: between 80 and 99.5%, trifluoromethanesulphonic acid: between 0.5 and 15%, water: between 0 and 5%.

2. Catalyst according to claim 1 wherein said support, before impregnation with said mixture, contains at most 2% of impurities.

3. Catalyst according to of claim 1 wherein said support is principally constituted by substantially spherical particles having a diameter of between 5 and 110 μm.

4. Catalyst according to claim 1 wherein said support is principally constituted by substantially spherical particles having a diameter of between 5 and 80 μm.

5. Catalyst according to claim 1 wherein the composition by weight of said mixture is between the following values:

sulphuric acid: between 85 and 99.5%, trifluoromethanesulphonic acid: between 0.8 and 15%, water: between 0.05 and 3%.

6. In an alkylation process which reacts a feedstock comprising at least one isoparaffin selected from the group consisting of isobutane and isopentane, with at least one olefin containing 3 to 6 carbon atoms per molecule, in the presence of a catalyst, the improvement wherein the catalyst is according to claim 1.

7. A process according to claim 6 wherein the reaction temperature is below 0° C.

8. A catalyst according to claim 1, wherein the acidic mixture is solid.

9. A catalyst according to claim 2, wherein the acidic mixture is solid.

10. A catalyst according to claim 3, wherein the acidic mixture is solid.

11. A catalyst according to claim 4, wherein the acidic mixture is solid.

12. A process according to claim 6, wherein the acidic mixture is solid.

13. A process according to claim 12, wherein the composition by weight of the acidic mixture is:

sulphuric acid: between 85 and 99.5%, trifluoromethanesulphonic acid: between 0.8 and 15%, water: between 0.05 and 3%.

14. A process according to claim 5, wherein the support of the catalyst has an average diameter of between 5 and 80 μm.

* * * * *